United States Patent [19]

Ogawa et al.

[11] 4,268,362
[45] May 19, 1981

[54] METHOD FOR PURIFYING ACETIC ACID

[75] Inventors: Tetsuya Ogawa, Futsushi; Norio Yoshizaki, Ichiharashi; Tadakatsu Katsuragi, Ichiharashi; Makoto Nakamura, Ichiharashi; Kiyonori Shiiba, Ichiharashi, all of Japan

[73] Assignee: Chisso Corporation, Osaka, Japan

[21] Appl. No.: 754,911

[22] Filed: Dec. 28, 1976

[30] Foreign Application Priority Data

Dec. 29, 1975 [JP] Japan ................................. 50-155982

[51] Int. Cl.³ .......................... B01D 3/00; C07C 51/44
[52] U.S. Cl. ....................................... 203/28; 203/71; 203/DIG. 19; 562/608
[58] Field of Search ............. 203/28, 29, 16, DIG. 19, 203/71; 260/541; 562/608

[56] References Cited

U.S. PATENT DOCUMENTS 2,186,617  1/1940  Othmer ................................. 203/28
3,838,018  9/1974  Gehrmann et al. ................. 260/541

Primary Examiner—Wilbur L. Bascomb, Jr.
Attorney, Agent, or Firm—Fred Philpitt

[57] ABSTRACT

A method for purifying raw acetic acid containing formaldehyde is provided wherein raw acetic acid is heat-treated at a temperature of about its boiling point or higher, in advance of the conventional distillation for removing a lower boiling fraction, and the acetic acid thus heat-treated is distilled to remove the lower boiling fraction, whereby the content of formaldehyde can be reduced down to 30 ppm or lower.

6 Claims, 2 Drawing Figures

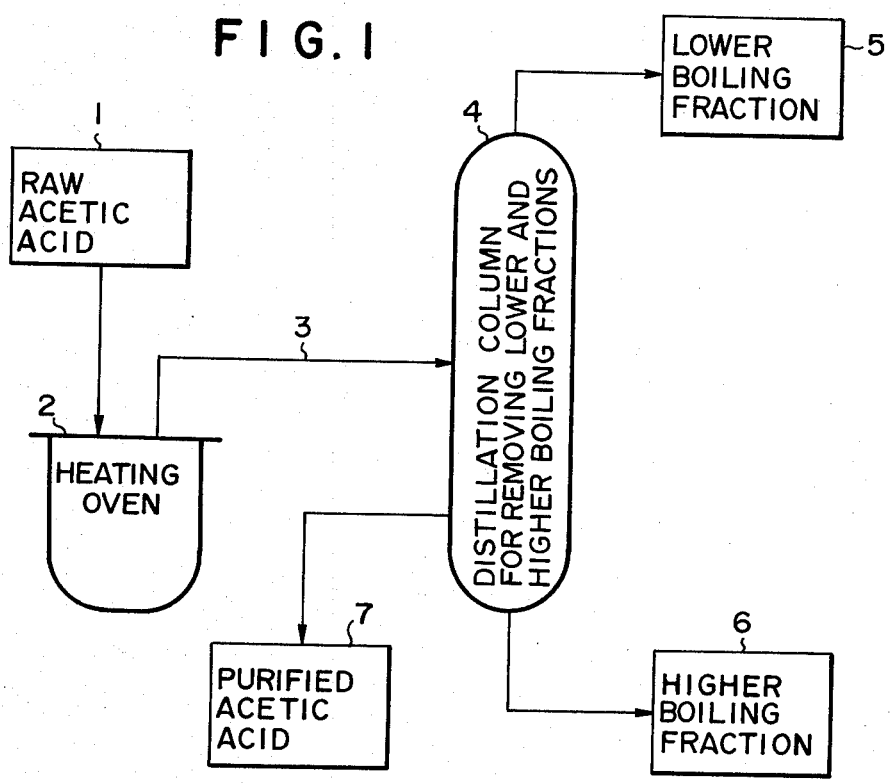
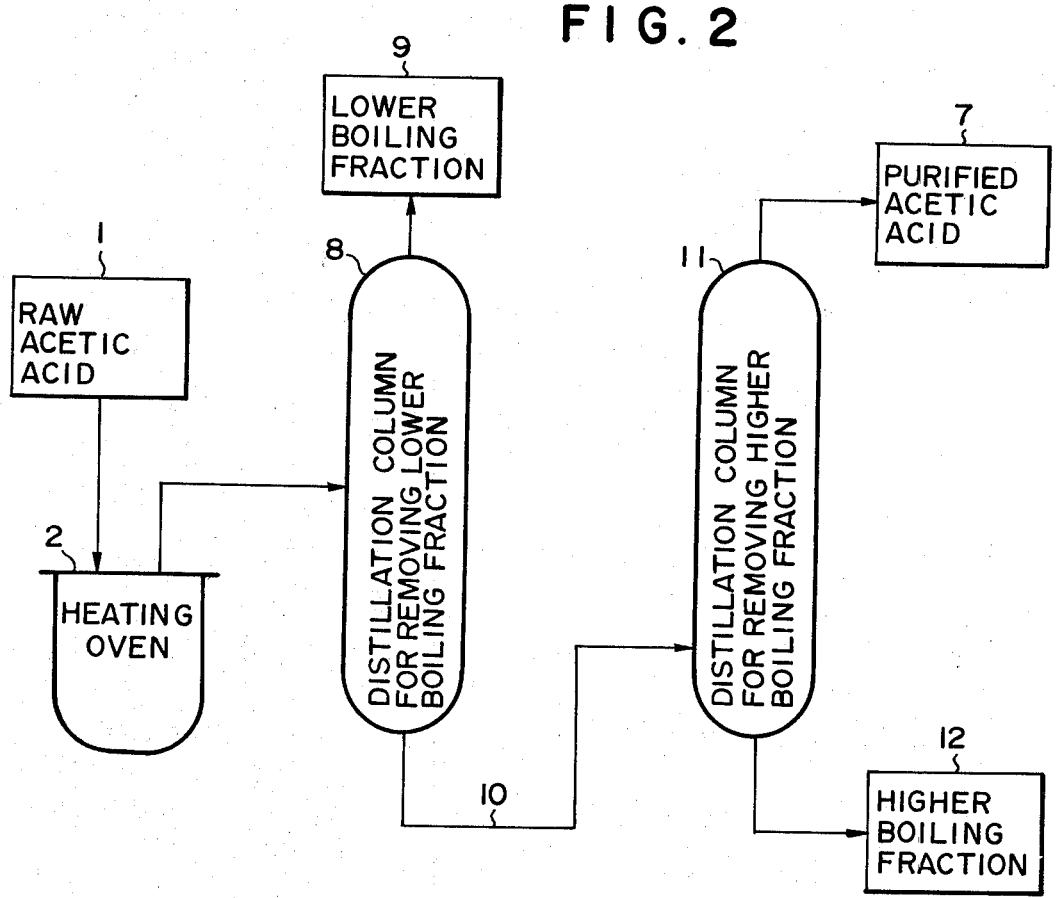

METHOD FOR PURIFYING ACETIC ACID

BACKGROUND OF THE INVENTION

The present invention relates to a method for purifying acetic acid by removing therefrom by-products such as formaldehyde by-produced in the production of acetic acid.

As for the method for producing acetic acid, various methods have been employed, such as the one which relies on oxidation of acetaldehyde, another one which relies on oxidation of hydrocarbons such as naphtha, butane or the like, a further one which relies on a synthesis from methanol and carbon monoxide, etc. In any of these methods, however, since various kinds of by-products are formed during the process of oxidation, etc., it is necessary to remove them. As for such by-products, aldehydes, formic acid, methyl alcohol, methyl acetate, etc. are mentioned although the kinds vary depending upon the methods for producing acetic acid. These by-products can be usually removed by purification through distillation, but it is difficult to remove reducible substances such as formic acid, formaldehyde, etc. by means of a mere distillation. For removing such by-products to obtain purified acetic acid, various methods have been also proposed such as treatment with an oxidizing agent e.g. potassium permanganate, etc., chemical treatment e.g. hydrogenation treatment, etc. followed by distillation, removal through azeotropic distillation with chloroform, benzene, etc. However, even in case of technical grade of acetic acid, it has become a recent tendency that acetic acid containing only an extremely small amount of impurities is required. Particularly for acetic acid for fermentation use, for example those employed in producing sodium glutamate, lysine, ribonucleic acid, etc., acetic acid which is used as a solvent in producing terephthalic acid, etc., it has now become necessary to determine the content of formaldehyde by way of a standard test for products, in addition to the past potassium permanganate test for determining reducible substances, and in this case, 30 ppm or less has become now a required value of the content. The prior art, however, has been directed only to removal or separation of reducible substances, particularly formic acid, and there is almost none which relates to removal of formaldehyde. Only Japanese Pat. No. 267113 discloses a method for separating formaldehyde by an azeotropic distillation in the presence of an auxiliary substance such as isopropyl acetate or the like. However, the content of formaldehyde in the acetic acid obtained by the purification according to this method is as high as 300–500 ppm. Such a value does not satisfy the above-mentioned requirement.

SUMMARY OF THE INVENTION

A first object of the present invention is to provide a commercial method for removing formaldehyde from raw acetic acid. A second object of the present invention is to provide acetic acid containing 30 ppm or less of formaldehyde. Other objects will be apparent from the description mentioned below.

In the purification of acetic acid through distillation, usually a lower boiling fraction is removed by topping, and distillation is carried out thereafter. However, according to the above-mentioned method or the like method, formaldehyde cannot be completely removed.

The present inventors have found that even when an acetic acid having removed a lower boiling fraction by distillation is redistilled, a considerable amount of formaldehyde is still contained in the resulting lower boiling fraction in the redistillation, and further the content of formaldehyde in the main fraction is also not reduced. The reason for this phenomenon is believed to be due to a further decomposition of higher molecular weight formaldehydes contained in the higher boiling fraction during the time of heating in the redistillation.

The present inventors further have found that when an acetic acid containing formaldehyde is distilled, the formaldehyde contained therein is separated and mixed into each of the resulting initial fraction (lower boiling fraction), main fraction and higher boiling fraction. The reason for this phenomenon is believed to be due to the fact that lower molecular weight formaldehydes are distilled off while being incorporated in the initial fraction and the main fraction, whereas such higher molecular weight formaldehydes are distilled off while being incorporated in the higher boiling fraction, and in this case there is an interchangeability between the lower molecular weight formaldehydes and the higher molecular weight formaldehydes.

The present inventors have made strenuous studies based upon these findings, and as a result further found that, in the case of an acetic acid obtained by maintaining in advance a raw acetic acid at a high temperature and thereafter removing a lower boiling fraction from the resulting acetic solution, even when it is redistilled, the resulting lower boiling fraction contains almost no formaldehyde and also the resulting main fraction contains only an extremely small amount of formaldehyde. Based upon this finding, the present inventors have succeeded in producing an acetic acid containing only an extremely small amount of formaldehyde.

The present invention resides in a method for purifying a raw acetic acid into an acetic acid whose formaldehyde content is 30 ppm or lower which comprises maintaining in advance a raw acetic acid at a temperature of about its boiling point or higher and thereafter removing by distillation a lower boiling fraction from the resulting acetic acid.

DETAILED DESCRIPTION OF THE INVENTION

The raw acetic acid to be employed in the method of the present invention has no particular limitation, but it may be those obtained by synthetic reactions such as oxidation of acetaldehyde, gas phase or liquid phase oxidation of butane, oxidation of petroleum naphtha of paraffins, reaction of methanol with carbon monoxide, etc., and it is preferable to employ an acetic acid in which the catalyst used in the synthetic reaction for producing acetic acid is remaining. As for the kinds of such catalysts, salts or complexes of transition metals, naphthenates, stearates, acetates or the like of Co, Mn, Fe, etc., complexes of compounds of rhodium or cobalt, etc. may be mentioned. The temperature and time employed in the heat-treatment carried out in advance in the method of the present invention also have no particular limitation, but if the heat-treatment is carried out at a temperature as high as about the boiling point of raw acetic acid or higher, preferably about 110° C. or higher, the time may be as short as about 10 minutes to several hours. As for preferable conditions, the temperature may be in the range of 130°–180° C. and the time may be in the range of 15–90 minutes. As for the heat-treating manner, the raw acetic acid may be heated under reflux at a given temperature and for a given time under the atmospheric pressure. However, in order to make the effectiveness of the present invention more remarkable, the acid may be heated at a higher temperature and hence under an elevated pressure.

Next, the succeeding removal of lower boiling fraction (or light ends) from the resulting acetic acid will be mentioned referring to the accompanying drawings.

FIG. 1 and FIG. 2 each show a schematic flow sheet of an embodiment of the present invention, wherein numeral 1 shows raw acetic acid; 7, purified acetic acid; 2, heating oven; 4, distillation column for removing lower and higher boiling fractions; 8, distillation column for removing lower boiling fraction (or light ends column); and 11, distillation column for removing higher boiling fraction.

As for a preferable manner, as shown in FIG. 1, raw acetic acid 1 is heat-treated in a heating oven 2. The resulting acid is fed into a feeding port located at an intermediate plate of a distillation column 4 for removing lower and higher boiling fractions, and a lower boiling fraction 5 is removed from the top of the column while a higher boiling fraction 6 is removed from the bottom. A purified acetic acid 7 is withdrawn from a taking-out port located below said feeding port. Further another preferable manner as shown in FIG. 2 may be also employed. A raw acetic acid heat-treated in a heating oven 2 is fed to an intermediate plate of a distillation column 8 for removing a lower boiling fraction, and a lower boiling fraction 9 is distilled off from the top of the column, while the resulting acetic acid is withdrawn from the bottom and fed through a leading pipe 10 to an intermediate plate of a distillation column 11 for removing a higher boiling fraction. A higher boiling fraction 12 is withdrawn from the bottom of the column while a purified acetic acid 7 is distilled off from the top. In the above-mentioned distillation for removing a lower boiling fraction, it is preferable to remove 5-15% by weight of lower boiling fraction based upon the weight of raw acetic acid fed.

Purified acetic acid for commercial uses obtained according to the method of the present invention contains 30 ppm or less of formaldehyde and is fully applicable to the above-mentioned uses.

According to the method of the present invention, since a raw acetic acid is heat-treated in advance of the distillation for removing lower boiling fraction, the formaldehyde contained in the original raw acetic acid is separated into lower molecular weight formaldehydes which are distilled off together with the lower boiling fraction and higher molecular weight formaldehydes which remain in the higher boiling fraction and has a property of being not decomposed at the time of re-heating (distillation for removing lower boiling fraction), whereby an acetic acid which, when distilled, contains almost no formaldehyde in the resulting main fraction, is obtained, and formaldehyde becomes completely separable in the step of distillation for removing lower boiling fraction. Further, when a raw acetic acid in which a catalyst employed in the synthetic reaction for obtaining acetic acid is remaining is employed, the heat-treatment of raw acetic acid in the method of the present invention can exhibit a more notable effectiveness, since the heat-treatment can inactivate the catalyst in the ability of decomposing the higher molecular weight formaldehydes.

The present invention will be further illustrated by way of non-limitative Examples and Comparative Examples.

EXAMPLE 1

Purification of a raw acetic acid was carried out in a manner as shown in FIG. 1.

A raw acetic acid 1 (acetic acid concentration: 95%, catalyst concentration: 0.02%, and formaldehyde concentration: 1,150 ppm) obtained by oxidation of acetaldehyde by air using manganese acetate as catalyst was maintained in a heating oven 2 at 138° C. under a pressure of 3.5 Kg/cm$^2$ for one hour. The resulting acetic acid was fed through a leading pipe 3 into the thirtieth plate of a distillation column 4 for removing lower and higher boiling fractions, having 50 plates, and distilled under the atmospheric pressure and in a reflux ratio of 10. Ten % by weight of a lower boiling fraction 5 based upon the weight of acetic acid fed was distilled off from the top of the column, while 2% by weight of a higher boiling fraction was withdrawn from the bottom, and an acetic acid 7 was withdrawn from a taking-out port located at the tenth plate. The content of formaldehyde in the acetic acid thus obtained was measured according to a colorimetric analysis method with sodium salt of chromotropic acid to give 11 ppm.

COMPARATIVE EXAMPLE 1

Example 1 was repeated except that the raw acetic acid 1 was not heated under the pressure in the heating oven 2. The content of formaldehyde in the resulting acetic acid was 90 ppm.

EXAMPLE 2

Purification of a raw acetic acid was carried out in a manner as shown in FIG. 2.

The same raw acetic acid 1 as employed in Example 1 was maintained under the same conditions as in Example 1. The resulting acetic acid was fed into the thirtieth plate of a distillation column 8 for removing lower boiling fraction having 50 plates, and distilled under the atmospheric pressure and in a reflux ratio of 10. Ten % by weight of a lower boiling fraction 9 based upon the weight of acetic acid fed was removed from the top of the column, while a high boiling fraction was withdrawn from the bottom and fed through a leading pipe 10 into the second plate of distillation column 11 for removing higher boiling fraction having 10 plates. A higher boiling fraction 12 in an amount corresponding to 4% by weight based upon the weight of acetic acid fed was withdrawn from the bottom of the column, while a purified acetic acid 7 was obtained at the top. The acetic acid thus obtained was analyzed according to the same method as in Example 1 to give a formaldehyde content of 16 ppm.

COMPARATIVE EXAMPLE 2

Example 2 was repeated except that the raw acetic acid was not heated in the heating oven 2. The content of formaldehyde in the resulting acetic acid was 80 ppm.

What is claimed is:

1. The method for substantially reducing the formaldehyde content of concentrated acetic acid which comprises
    (a) feeding a solution containing at least 95% raw acetic acid obtained from a synthetic reaction and having a formaldehyde content substantially greater than 30 ppm into a heating zone, said synthetic reaction being selected from the group consisting of the oxidation of acetaldehyde, the oxidation of butane, and oxidation of naphtha and the reaction of methanol with carbon monoxide,
(b) maintaining said raw acetic acid in said heating zone at a temperature at about the boiling point of the acetic acid or higher,
(c) removing the heated product from step (b) and delivering it to a distillation zone, and
(d) operating said distillation zone so as to obtain
(1) a lower boiling fraction,
(2) a higher boiling fraction; and
(3) an intermediate acetic acid fraction that has a boiling point intermediate said lower and higher boiling fractions, said intermediate acetic acid fraction having a formaldehyde content of 30 ppm or lower.

2. The method according to claim 1 wherein the temperature in step (b) is about 110° C. or higher.

3. The method according to claim 1 wherein the temperature in step (b) is in the range of about 130° to 180° C.

4. The method according to claim 1 wherein the said raw acetic acid is maintained in said heating zone for between ten minutes and several hours.

5. The method according to claim 1 wherein the raw acetic acid is maintained in said heating zone for 15 to 90 minutes.

6. A method according to claim 1 wherein said step (b) is carried out under an elevated pressure.

* * * * *